United States Patent
Wigginton

(10) Patent No.: US 10,405,889 B2
(45) Date of Patent: Sep. 10, 2019

(54) COLD FORGED CUTTING TIP FOR ORTHOPEDIC WIRES AND PINS

(71) Applicant: New Standard Device, LLC, San Antonio, TX (US)

(72) Inventor: Robert E. Wigginton, McKinney, TX (US)

(73) Assignee: New Standard Device, LLC, San Antonio, TX (US)

( * ) Notice: Subject to any disclaimer, the term of this patent is extended or adjusted under 35 U.S.C. 154(b) by 0 days.

(21) Appl. No.: 16/008,137

(22) Filed: Jun. 14, 2018

(65) Prior Publication Data

US 2018/0317967 A1    Nov. 8, 2018

(51) Int. Cl.
| | |
|---|---|
| *A61B 17/66* | (2006.01) |
| *A61B 17/60* | (2006.01) |
| *A61B 90/10* | (2016.01) |
| *A61B 90/00* | (2016.01) |
| *A61B 17/00* | (2006.01) |
| *A61B 17/62* | (2006.01) |
| *A61B 90/94* | (2016.01) |

(52) U.S. Cl.
CPC ............ *A61B 17/66* (2013.01); *A61B 17/60* (2013.01); *A61B 90/10* (2016.02); *A61B 17/62* (2013.01); *A61B 90/39* (2016.02); *A61B 90/94* (2016.02); *A61B 2017/00526* (2013.01)

(58) Field of Classification Search
CPC ............... A61B 17/866; A61B 17/58–17/6491
See application file for complete search history.

(56) References Cited

U.S. PATENT DOCUMENTS

| | | | | |
|---|---|---|---|---|
| 3,602,218 A | * | 8/1971 | Riordan | A61B 17/68 206/363 |
| 4,050,528 A | * | 9/1977 | Foltz | A61B 17/1628 173/170 |
| 4,127,119 A | * | 11/1978 | Kronner | A61B 17/62 606/56 |
| 4,157,714 A | * | 6/1979 | Foltz | A61B 17/1628 408/228 |
| 4,312,336 A | * | 1/1982 | Danieletto | A61B 17/6458 403/137 |
| 4,365,624 A | * | 12/1982 | Jaquet | A61B 17/62 606/56 |
| 4,373,518 A | * | 2/1983 | Kaiser | A61B 17/1615 606/329 |
| 4,541,422 A | * | 9/1985 | de Zbikowski | A61B 17/645 403/167 |
| 4,615,338 A | * | 10/1986 | Ilizarov | A61B 17/62 606/58 |
| 4,718,908 A | | 1/1988 | Wigginton et al. | |
| 4,775,426 A | | 10/1988 | Murley et al. | |

(Continued)

*Primary Examiner* — Eduardo C Robert
*Assistant Examiner* — Michelle C Eckman
(74) *Attorney, Agent, or Firm* — Gregory K. Goshorn; Greg Goshorn, P.C.

(57) ABSTRACT

Provided are orthopedic wires and pins with a cold forged tip for use with External Bone Fixation (EBF) devices. Orthopedic wires includes a length of wire or bar stock and a cutting tip on an end of the length of the wire or bar stock, the cutting tip comprising a cold forged section, wherein a width of the cold forged section conforms to a diameter of the wire or bar stock; and a first plurality of cutting edges in the cold forged section. Also provided are techniques for the manufacture of orthopedic wires and pins.

6 Claims, 7 Drawing Sheets

(56) References Cited

U.S. PATENT DOCUMENTS

| | | | | |
|---|---|---|---|---|
| 4,978,348 A * | 12/1990 | Ilizarov | ............. | A61B 17/6425 |
| | | | | 606/105 |
| 5,431,652 A * | 7/1995 | Shimamoto | ............ | A61B 17/58 |
| | | | | 606/76 |
| 5,700,113 A * | 12/1997 | Stone | ......................... | B21J 5/12 |
| | | | | 408/1 R |
| 5,702,389 A * | 12/1997 | Taylor | ................... | A61B 17/62 |
| | | | | 606/56 |
| 5,971,984 A * | 10/1999 | Taylor | ................... | A61B 17/62 |
| | | | | 128/898 |
| 5,981,619 A * | 11/1999 | Shikinami | ............... | A61L 27/46 |
| | | | | 264/320 |
| 6,099,529 A * | 8/2000 | Gertzman | .......... | A61B 17/8605 |
| | | | | 606/309 |
| 6,159,210 A * | 12/2000 | Voor | .................. | A61B 17/6433 |
| | | | | 606/56 |
| 2001/0034520 A1 * | 10/2001 | Enayati | ............. | A61B 17/8635 |
| | | | | 606/59 |
| 2002/0029043 A1 * | 3/2002 | Ahrens | ............... | A61B 17/866 |
| | | | | 606/309 |
| 2002/0182565 A1 * | 12/2002 | Senia | ....................... | A61C 5/42 |
| | | | | 433/102 |
| 2006/0084997 A1 * | 4/2006 | Dejardin | ............ | A61B 17/1725 |
| | | | | 606/62 |
| 2006/0234800 A1 * | 10/2006 | Horimura | ................ | B21C 1/00 |
| | | | | 470/11 |
| 2007/0101797 A1 * | 5/2007 | Quan | ....................... | A61C 3/02 |
| | | | | 72/416 |
| 2007/0173834 A1 * | 7/2007 | Thakkar | ............. | A61B 17/7208 |
| | | | | 606/62 |
| 2008/0221681 A1 * | 9/2008 | Trieu | ................... | A61B 17/866 |
| | | | | 623/11.11 |
| 2009/0005871 A1 * | 1/2009 | White | ................... | A61B 17/562 |
| | | | | 623/17.11 |
| 2009/0149890 A1 * | 6/2009 | Martin | ............... | A61B 17/1717 |
| | | | | 606/316 |
| 2010/0030105 A1 * | 2/2010 | Noishiki | ............. | A61B 10/025 |
| | | | | 600/567 |
| 2012/0221005 A1 * | 8/2012 | Corneille | ........... | A61B 17/1631 |
| | | | | 606/62 |
| 2016/0089194 A1 * | 3/2016 | Diaz | .................. | A61B 17/8897 |
| | | | | 606/54 |
| 2016/0256208 A1 * | 9/2016 | Weinberg | ................ | C22C 23/00 |
| 2016/0287300 A1 * | 10/2016 | McCormick | ....... | A61B 17/7225 |
| 2017/0252069 A1 * | 9/2017 | Muniz | ................ | A61B 17/6483 |
| 2018/0093012 A1 * | 4/2018 | Ishikawa | ................ | A61L 31/14 |
| 2018/0132897 A1 * | 5/2018 | Shiner | ................ | A61B 17/6466 |
| 2018/0271573 A1 * | 9/2018 | Martin | ............... | A61B 17/8635 |

* cited by examiner

COLD FORGED CUTTING TIP FOR ORTHOPEDIC WIRES AND PINS

FIELD OF THE DISCLOSURE

The claimed subject matter relates to cold forged orthopedic wires and pins, and the manufacture thereof.

BACKGROUND

External Bone Fixation (EBF) devices, or systems, are employed in the treatment of bone deformity and acute trauma. One well-known reconstructive system is the Ilizarov frame, as shown in U.S. Pat. Nos. 4,365,624; 4,615,338; 4,978,348; 5,702,389 and 5,971,984. The Ilizarov frame uses a combination of circular frames, pins and wires for deformity correction.

Typical EBF devices are affixed to a patient's bone with a combination of pins and wires. Currently wires used in conjunction with EBF systems are typically manufactured using 316 LVM stainless steel, which is a very mild steel.

SUMMARY

Provided are orthopedic wires and pins with cold forged tips and the manufacture thereof. Orthopedic wires and pins are employed in conjunction with External Bone Fixation (EBF) devices, which are used to fix broken bones and to stabilize bones that are being corrected or healing. The typical steel employed in orthopedic wires and pins is 316 LVM stainless steel, which is a very mild steel that does not hold a cutting edge well. If the cutting tip of an orthopedic wire or pin does not hold up, it becomes dull or blunt when drilling the bone, potentially resulting in thermal necrosis, bone damage and burnt soft tissue that may result in infections.

Provided are orthopedic wires and pins with a cold forged tip for use with External Bone Fixation (EBF) devices. An orthopedic wire includes a length of wire and a cutting tip on an end of the length of wire, the cutting tip comprising a cold forged section, wherein a width of the cold forged section conforms to a diameter of the length of wire; and a first plurality of cutting edges in the cold forged section.

An orthopedic pin includes a length of bar stock and a cutting tip on an end of the length of bar stock, the cutting tip comprising a cold forged section, wherein a width of the cold forged section conforms to a diameter of the length of the bar stock; and a first plurality of cutting edges in the cold forged section. Also provided are techniques for the manufacture of the claimed orthopedic wires and pins.

This summary is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed description.

BRIEF DESCRIPTION OF THE DRAWINGS

A better understanding of the claimed subject matter can be obtained when the following detailed description of the disclosed embodiments is considered in conjunction with the following figures, in which:

DETAILED DESCRIPTION OF THE FIGURES

The illustrations and diagrams in the Figures illustrate the architecture, functionality, and operation of possible implementations of systems according to various embodiments of the present invention.

Figure 1:
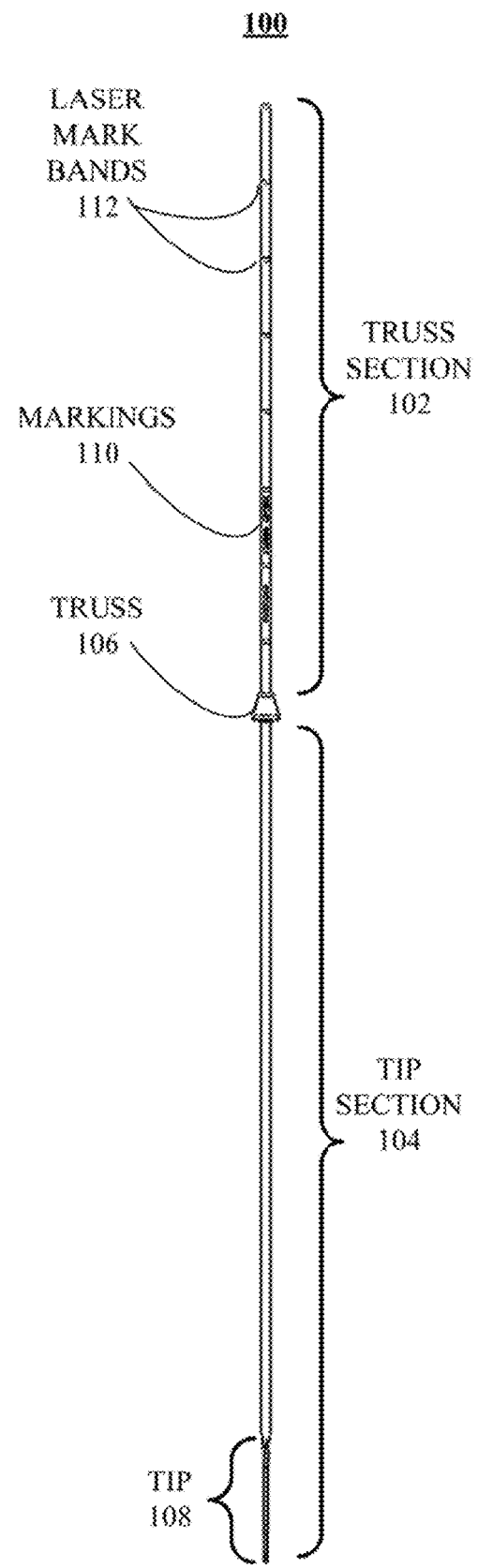
FIG. 1 is an illustration of an orthopedic wire manufactured in accordance with the disclosed technology.

Turning now to the figures, FIG. 1 is a block diagram of an example of an orthopedic wire 100 manufactured in accordance with the disclosed technology. Although described with reference to orthopedic wires, the following description is equally applicable to orthopedic pins. Both orthopedic wires and orthopedic pins are typically made of 316 LVM stainless steel. For the sake of this disclosure, wires are defined as having a diameter less than one and eight tenths millimeters (1.8 mm.) and pins having a diameter greater than 1.8 mm, and typically, but not necessarily, less than six and one-half millimeters (6.5 mm).

Orthopedic wire 100, which is typically manufactured from a single length of wire, is labeled as two sections, a truss section 102 and a tip section 104 with a truss 106 defining the point at which sections 102 and 104 meet. Sections 102 and 104 are labeled merely to provide a reference to different ends of orthopedic wire 100. It should be understood that truss 106 is not necessary and the disclosed orthopedic wires and pins may be constructed without a truss such as truss 106. An end of tip section 104 opposite truss section 102 comprises a cold forged tip 108. Cold forged tip 108 is described in more detail below in conjunction with FIG. 2. The process of manufacturing orthopedic wire 100 generally and cold forged tip 108 more specifically is described in detail below in conjunction with FIGS. 5 and 6.

Truss section 102 includes laser mark bands 112, only two of which are labeled for the sake of simplicity. Laser mark bands 112 provide a Health Care Provider (HCP) an indication to a Health Care Provider (HCP) to the direction that orthopedic wire 100 should be pulled when wire 100 is being removed from a patient's limb and an External Bone Fixation (EBF) device (see 402, FIG. 7). This mitigates the possibility that the HCP may inadvertently attempt to pull truss 106 through the bone to which orthopedic wire 100 has been affixed. Truss section 102 also includes markings 110. Markings 110 may include, but are not limited to, the name of a company that manufactures or sells orthopedic wire 100, an indication of the type of material from which orthopedic wire 100 is manufactured, a lot number, a part number and a description of orthopedic wire 100.

Figure 2:
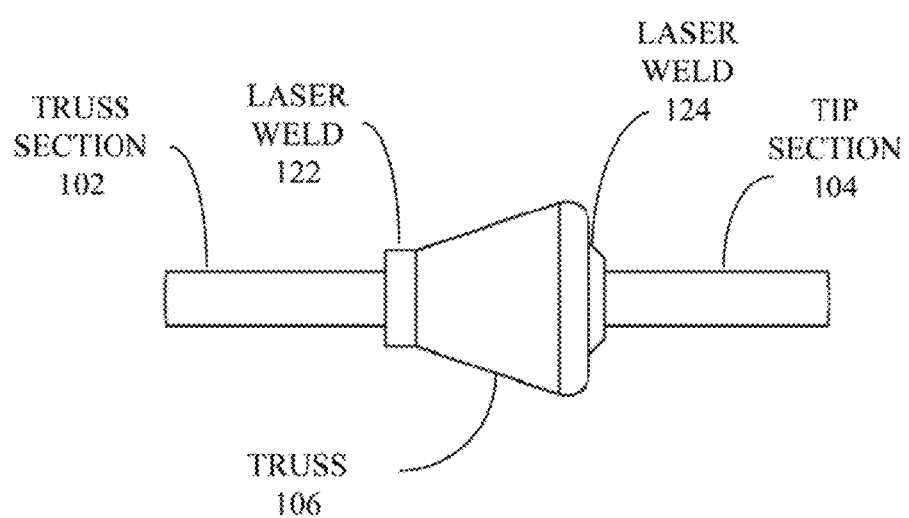
FIG. 2 is an illustration of a truss, first introduced in FIG. 1.
Figure 7:
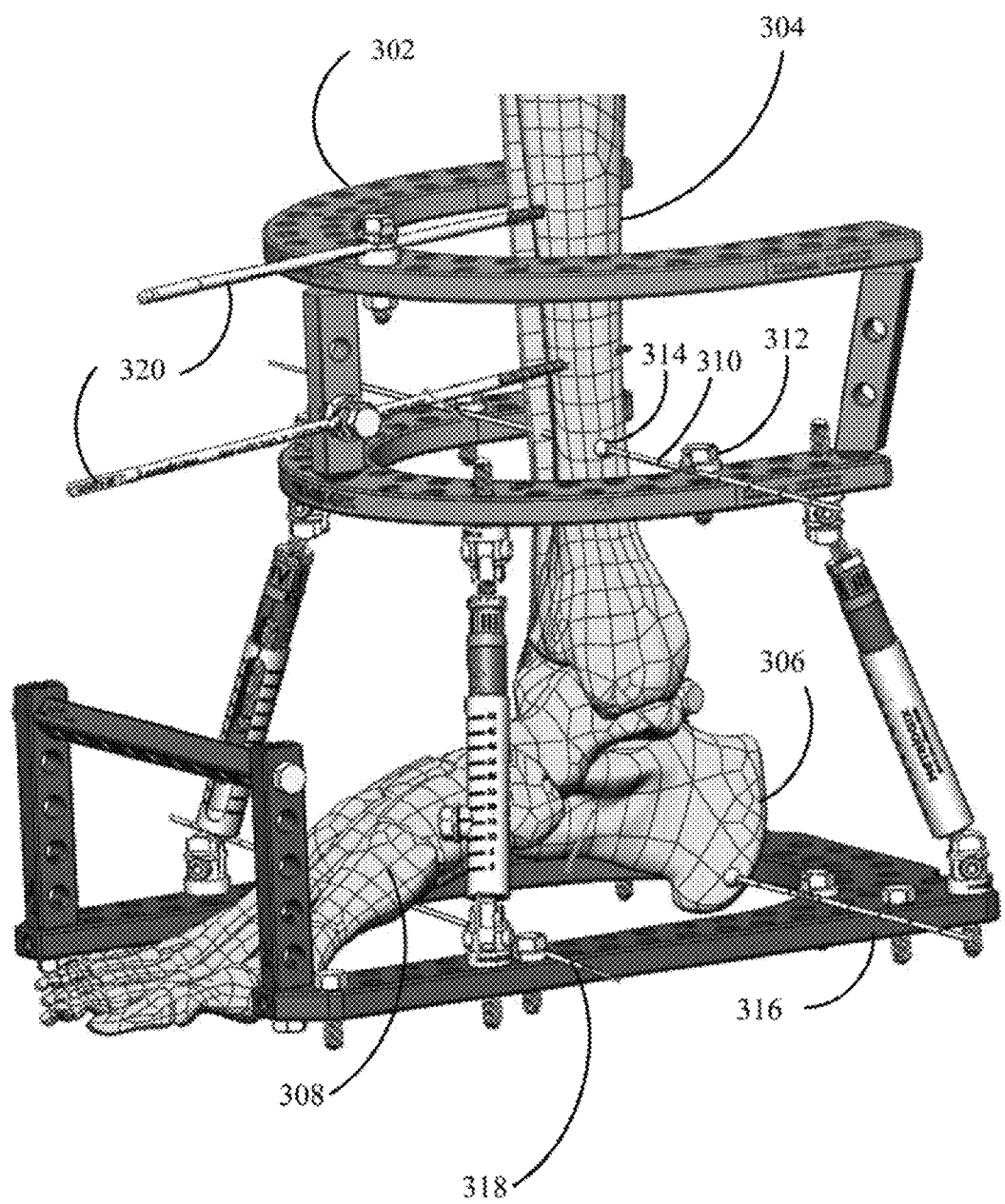
FIG. 7 is an illustration of orthopedic wires and pins manufactured in accordance with the disclosed technology employed to attach an External Bone Fixation (EBF) device to a patient's foot and leg bones.

FIG. 2 is an illustration of truss 106, first introduced in FIG. 1, in greater detail. In this example, truss 106 is positioned between truss section 102 (FIG. 1) and tip section 104 (FIG. 1). A laser weld 122 couples truss 106 to truss section 102 and a laser weld 124 couples truss 106 to tip section 104. Although illustrated as connected to truss section 102 and tip section 104 with laser welds 122 and 124, respectively, those with skill in the relevant arts should be able to think of multiple different methods of attachment. Truss 106 is permanently affixed to wire 100 (FIG. 1). Truss 106 is employed as a buttress to prevent a bone from moving when more than one wire is used to hold a bone in place within an EBF device. Wire 100 is typically attached to an EBF device such as EBF device 402 at two (2) points (see 310, 316 and 318. FIG. 7) with fixation bolts (see 312. FIG. 7).

Figure 3:
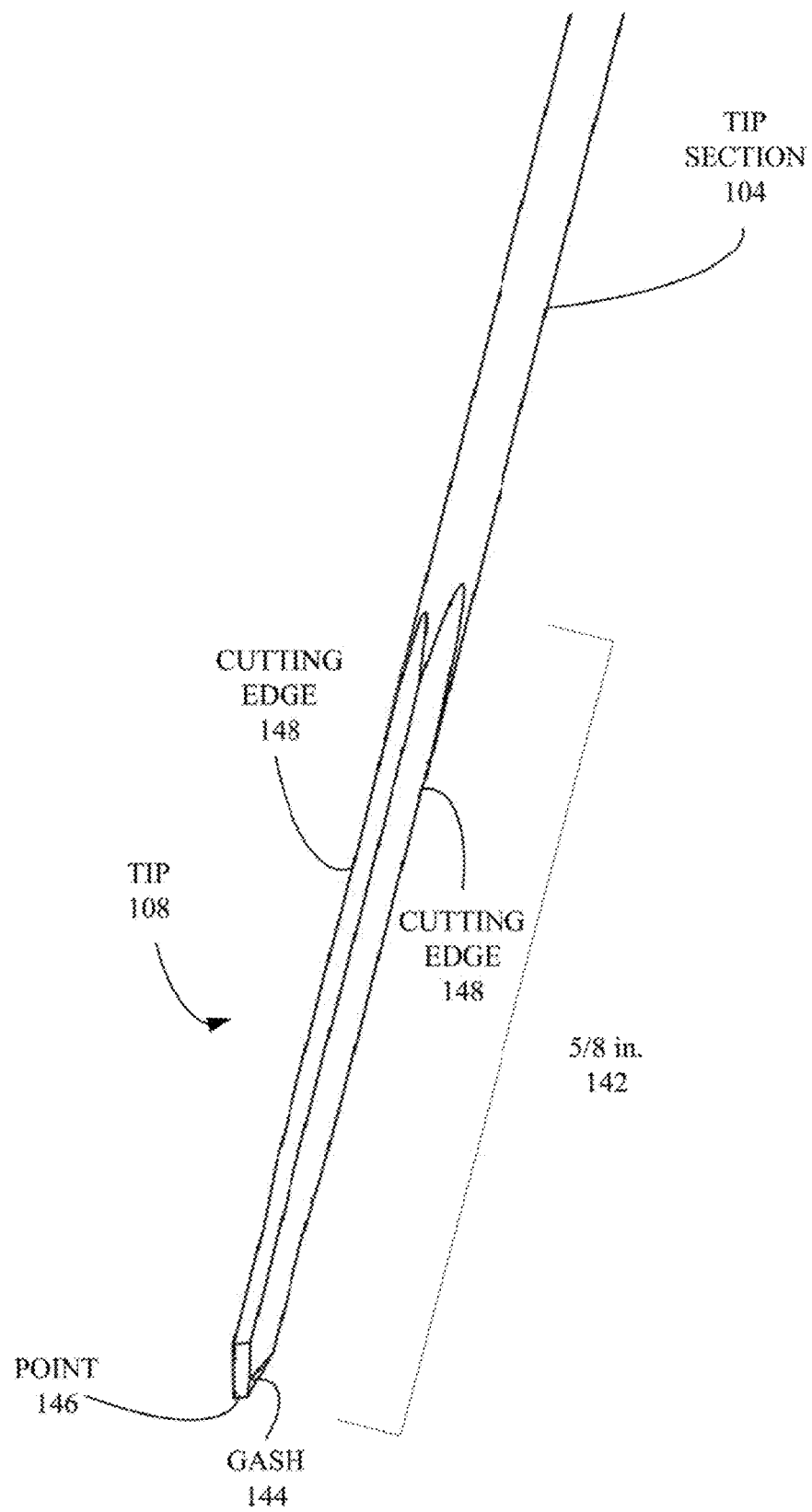
FIG. 3 is an illustration of a tip section of the orthopedic wire of FIG. 1 in greater detail.

FIG. 3 is an illustration of tip section 104 (FIG. 1) of orthopedic wire 100 (FIG. 1) in more detail. FIG. 3 shows a portion of tip section 104 that includes tip 108. In this example, tip 108, has a length 142 from a point 146 to the top of tip 108 of approximately five eighths of an inch (⅝ in.). The precise length of tip 108 is not critical to the claimed subject matter. At the point 146 end of tip 108 is a gash 144. Gash 144 is described in more detail below in conjunction with FIG. 4. Also illustrated are two (2) cutting edges 148, which are also described in more detail below in conjunction with FIG. 4.

Figure 4:
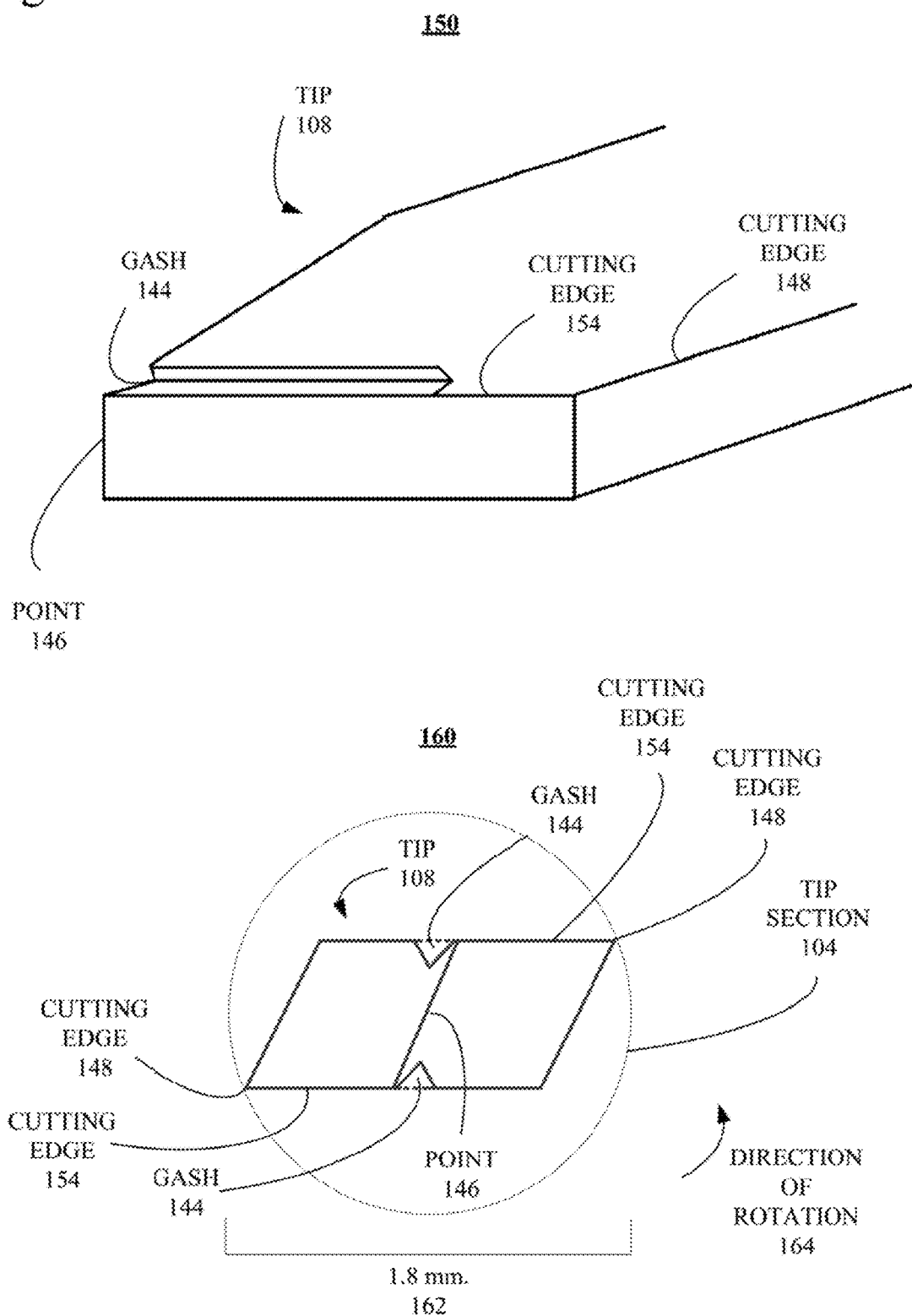
FIG. 4 is the end of the tip section of FIG. 2 in more detail.

FIG. 4 is the end of the tip section of FIG. 3 in more detail, specifically from two different perspectives 150 and 160. Perspective 150 shows an angled side view of tip 108 (FIGS. 1 and 2), gash 144 (FIG. 3), cutting edge 148 and a cutting edge 154. Also illustrated is point 146 (FIG. 3), of tip 108. It should be understood that perspective 150 only illustrates one side of tip 108 and that there is a gash 144, a cutting edge 148 and a cutting edge 154 on the opposite side of tip 108 that are not visible from this perspective.

Perspective 160 shows tip 108 from the perspective of looking straight on at point 146. Gash 144, point 146, cutting edge 148 and cutting edge 154 are visible. Unlike perspective 150, a second gash 144, cutting edge 148 and cutting edge 154 are visible. In this example, tip section 104 has a diameter 162 of approximately one and eight tenths millimeters (1.8 mm). A direction of rotation 164 illustrates the rotation applied to orthopedic wire 100 (FIG. 1) during insertion into a patient's bone.

Figure 5:
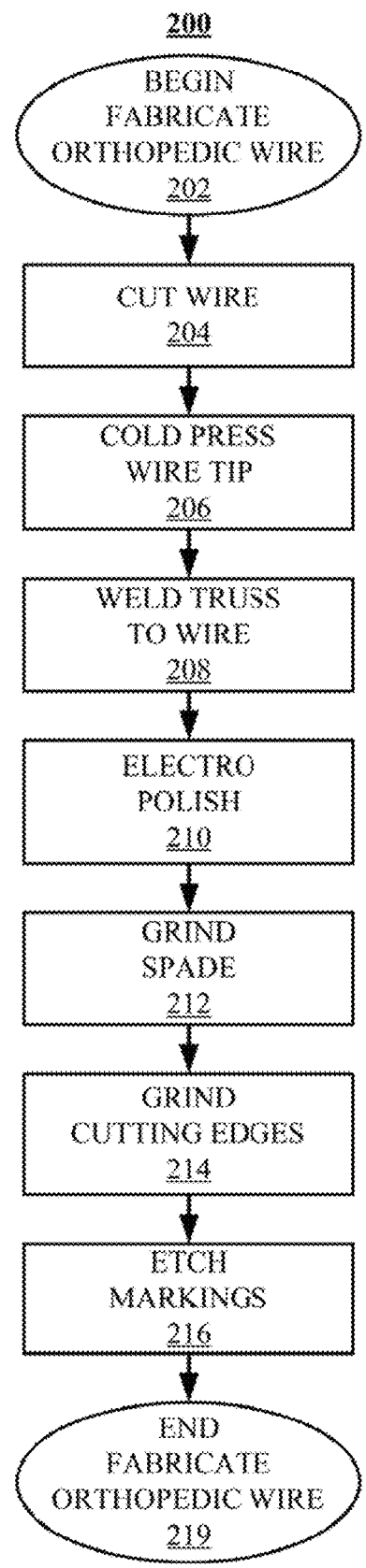
FIG. 5 is a flowchart of a Fabricate Orthopedic Wire process employed in the manufacture of the orthopedic wire of FIG. 1.

FIG. 5 is a flowchart of a Fabricate Orthopedic Wire process 200 employed in the manufacture of orthopedic wire 100 of FIG. 1. Although described in conjunction with the manufacture of wire 100, the described process is equally applicable to the manufacture of an orthopedic pin.

Process 200 starts in a "Begin Fabricate Orthopedic Wire" block 202 and proceeds immediately to a "Cut Wire" block 204. During processing associated with block 204, a piece of wire or bar stock approximately four hundred twenty millimeters (420 mm) is cut, typically from a spool of wire or from round bar stock. Typically, the wire is typically not longer than six hundred millimeters (600 mm). In the disclosed embodiment, the wire is typically medical grade 316 LVM stainless steel and approximately one and eight tenths millimeters (1.8 mm) in diameter, although those with skill in the relevant arts should appreciate that other types and diameters of medical grade steel might also be appropriate. The cut wire is referred to as a "blank." The blank is checked for straightness, i.e., it should roll on a smooth surface, and adjusted as needed.

During processing associated with a "Cold Press Wire Tip" block 206, one end of the wire cut during processing associated with block 204 is cold pressed. The cold pressed end ultimately becomes tip 108 (FIGS. 1, 3 and 4) of wire 100 (FIG. 1). A force of approximately six tons per square inch is applied to approximately five-eighths inches (⅝ in.) (see 142, FIG. 3) at the end of the cut wire or blank. This pressure flattens the end of what is referred as tip section 104 (FIG. 1) into a "lollipop" or "spade." (see 224, FIG. 6). Spade 224 is approximately one-half (½) as thick as the cut wire, i.e., 0.9 mm for spade 224 as opposed to 1.8 mm for the cut wire (see 162, FIG. 4). The cold press forging increases the hardness of the steel in spade 224 from approximately twelve to sixteen on the Rockwell Hardness Scale (12-16 Rc) to twenty-eight to thirty-two (28-32) Rc. The increased hardness and strength makes tip 108 harder, and thus able to hold a better cutting edge.

During processing associated with a "Weld Truss to Wire" block 208, truss 106 (FIGS. 1 and 2) is slid over the truss section 102 (FIG. 1) end of the orthopedic wire under process, positioned and affixed to orthopedic wire with laser welds 122, 124 (FIG. 2). It should be understood that in addition to laser welding truss 106 may be affixed to wire 100 by gluing, silver soldering, crimping, conventional welding, machining from bar stock the approximate diameter of the bar stock or otherwise affixed to wire 100. During processing associated with a "Electro Polish" block 210, the entire orthopedic wire 100, including spade 224 and truss 106, is electro polished to produce a smooth finish. During processing associated with a "Grind Spade" block 212, spade 224 undergoes a grinding process in which the sides of spade 224 are ground off to conform to the diameter of the blank, or approximately 1.8 mm.

During processing associated with a "Grind Cutting Edges" block 214, tip 108 is machined into the end of the blank under process. First, a first set of cutting edges 148 (FIGS. 3 and 4), with a relief angle (not shown), are ground into the edge of what is left of spade 224. Cutting edges 148 are typically ground to industry standards, or approximately sixty degrees (60°). This provides the blank under processing to have side cutting edges 148. Second, a second set of ninety degree (90°) cutting edges 154, with cutting edges and relief angles (not shown), are ground into the tip (see point 146, FIG. 4) of that which remains of spade 224. Third, gashes 144 (FIG. 3) are ground into the cutting edge of point 146 to sharpen point 146. The grinding described in conjunction with blocks 212 and 214 produces five (5) cutting edges, i.e., two (2) cutting edges 148, two (2) cutting edges 154 and one (1) cutting edge at point 146.

During processing associated with an "Etch Markings" block 216, markings 110 (FIG. 1) are etched into truss section 102 of the blank under process. Finally, process 200 proceeds to an "End Fabricate Orthopedic Wire" block 219 and the manufacturing of orthopedic wire 100 (FIG. 1) is complete. It should be noted that the process described above provides an orthopedic wire that is able to cut a patient's bone when inserted rather than scraping the bone like currently existing trocar tip orthopedic wires.

Figure 6:
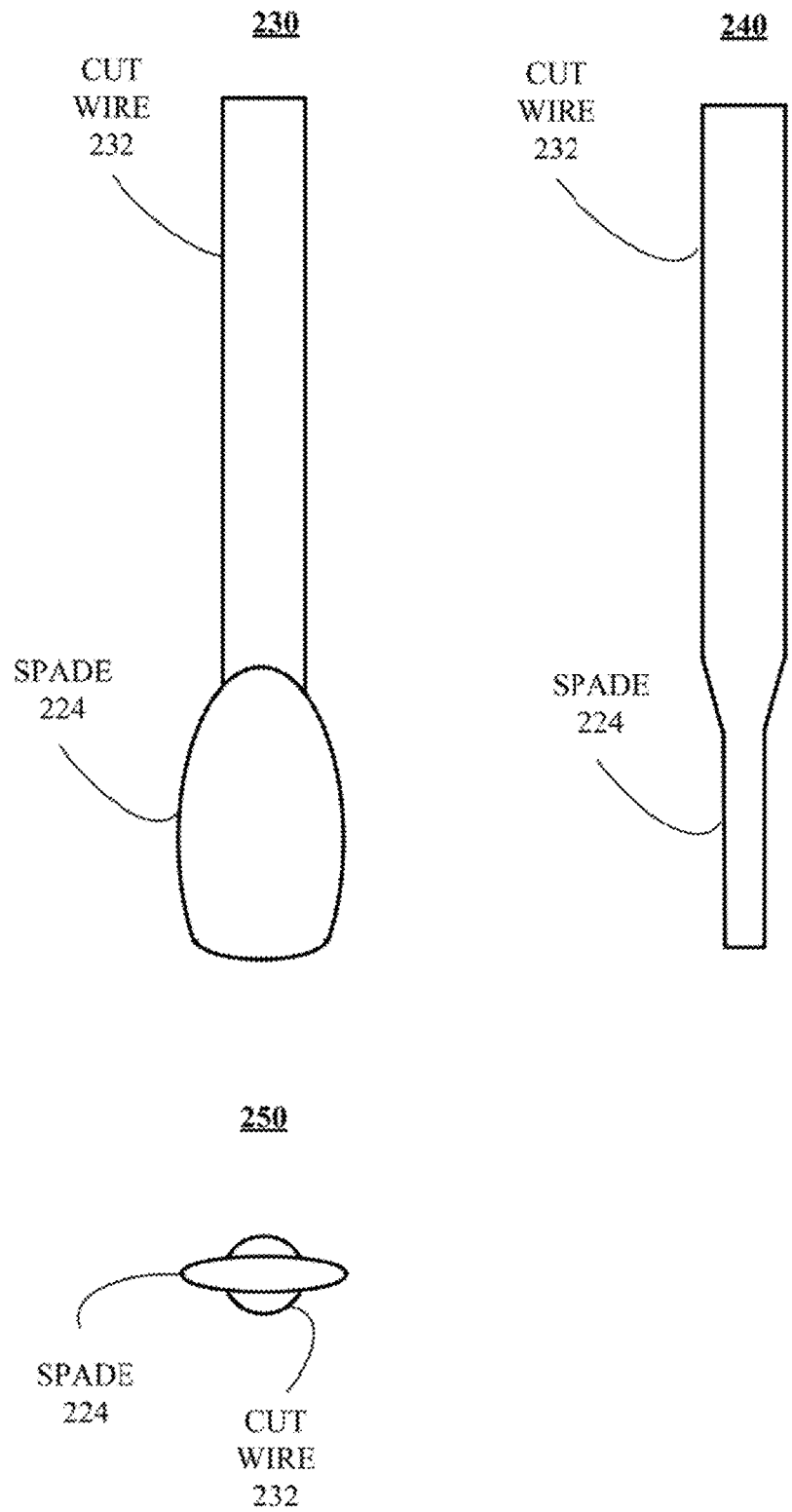
FIG. 6 is an illustration of a tip of the orthopedic wire of FIG. 1 in one stage of production.

FIG. 6 is an illustration of different perspectives 230, 240 and 250 of that which ultimately becomes tip 108 (FIGS. 1, 3 and 4) of orthopedic wire 100 of FIG. 1 at one point of production, specifically between Cold Press Point block 206 and Grind Spade block 212 of FIG. 5. As explained above in conjunction with FIG. 5, the end of a cut wire or bar stock, or blank, 232 corresponding to that which ultimately becomes tip 108 (FIGS. 1, 3 and 4) (see 204, FIG. 5) is cold pressed to form spade 224 (see 206, FIG. 5). Perspective 230 shows cut wire 232 so that the flattened edge of spade 224 is visible. Perspective 240 shows cut wire 232 rotated ninety degrees (90°). Perspective 250 shows cut blank from the end of perspective 230.

FIG. 7 is an illustration of orthopedic wires such as orthopedic wire 100 (FIG. 1) manufactured in accordance with the disclosed technology employed to attach an External Bone Fixation (EBF) device 302 to a patient's foot bone, which includes a leg bone 304, an ankle bone 306 and a foot bone 308. An orthopedic wire 310, like orthopedic wire 100 (FIG. 1), is attached to EBF device 302 with a joint or hinge 312 and attaches EBF device 302 to leg bone 304. A truss 314 positions orthopedic wire 310 against leg bone 304. In a similar fashion, an orthopedic wire 316 attaches EBF device 302 to ankle bone 306.

An orthopedic wire 318, which unlike orthopedic wire 100 does not include truss 106, passes through foot bone 308 and attaches to EBF device 302 with fixation bolts at two points. EFS device 302 is also attached to leg bone 304 with two (2) pins 320, manufactured in accordance with the claimed subject matter.

While the claimed subject matter has been shown and described with reference to particular embodiments thereof, it will be understood by those skilled in the art that the foregoing and other changes in form and detail may be made therein without departing from the spirit and scope of the claimed subject matter, including but not limited to additional, less or modified elements and/or additional, less or modified blocks performed in the same or a different order.

I claim:

1. A method for the manufacture of an orthopedic wire for attaching an external bone fixation device (EBF) to a patient, comprising:
   cutting a wire to produce a length of wire;
   cold forging a tip of the length of wire to approximately one half the diameter of the wire to form a spade;
   grinding two edges of the spade so that the diameter of the spade conforms to the diameter of the length of wire; and
   grinding first cutting edges into each edge of the spade that remains once the two edges have been ground.

2. The method of claim 1, further comprising grinding a cutting point into the tip of the spade that remains.

3. The method of claim 1, further comprising grinding a second plurality of cutting edges into the first plurality of cutting edges so that each cutting edge of the second plurality of cutting edges is in a corresponding cutting edge of the first plurality of cutting edges.

4. A method for the manufacture of a fixation device for attaching an external bone fixation device (EBF) to a patient, comprising:
   cutting a bar of to produce a pin;
   cold forging a end of the pin in to approximately one half the diameter of the pin to form a spade;
   grinding two edges of the spade so that the diameter of the spade conforms to the diameter of the pin; and
   grinding first cutting edges into each edge of the spade that remains once the two edges have been ground.

5. The method of claim 4, further comprising grinding a cutting point into the tip of the spade of the pin that remains.

6. The method of claim 4, further comprising grinding a second plurality of cutting edges into the first plurality of cutting edges so that each cutting edge of the second plurality of cutting edges is in a corresponding cutting edge of the first plurality of cutting edges of the spade of the pin.

* * * * *